US006348567B1

(12) United States Patent
Krystal et al.

(10) Patent No.: US 6,348,567 B1
(45) Date of Patent: *Feb. 19, 2002

(54) PEPTIDES AND THEIR USE TO AMELIORATE CELL DEATH

(75) Inventors: Gerald Krystal; Simon W. Rabkin, both of Vancouver (CA)

(73) Assignee: CV Molecular Therapeutics Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/294,457

(22) Filed: Apr. 19, 1999

Related U.S. Application Data

(63) Continuation-in-part of application No. 08/759,599, filed on Dec. 5, 1996, now Pat. No. 5,917,013.
(60) Provisional application No. 60/008,233, filed on Dec. 6, 1995.

(51) Int. Cl.$^7$ .............................. C07K 7/06; C07K 7/08; C07K 14/00
(52) U.S. Cl. ....................... 530/300; 530/317; 530/326; 530/327; 530/329
(58) Field of Search ................................ 514/2, 13, 14, 514/15, 16, 17; 530/300, 326, 327, 328, 329, 317

(56) References Cited

U.S. PATENT DOCUMENTS 5,917,013 A  6/1999  Rabkin et al. .............. 530/300

FOREIGN PATENT DOCUMENTS

WO  WO 94/07992  4/1994

OTHER PUBLICATIONS

Fung et al.,"Beneficial Effects of Streptokinase on Left Ventricular Function After Myocardial Reoxygenation and Reperfusion Following Global Ischemia in the Isolated Rabbit Heart," *J. Cardiovasc. Pharmacol.* 6(3):429–435, 1984.

Jackson and Tang, "Complete Amino Acid Sequence of Streptokinase and Its Homology with Serine Protease," *Biochemistry* 21:6620–6625, 1982.

Kurl, *Spectrum: Therapy Markets and Emerging Technologies*, Decision Resources, Inc., Waltham, Massachusetts, Aug. 18, 1994, "Apoptosis: A New Therapeutic Approach to Cell–Based Disorders."

Mickelson et al., "Protection of Myocardial Function and Coronary Vasculature by Streptokinase," *J. Cardiovasc. Pharmol.* 12(2):186–195, 1988.

Rabkin, "Streptokinase But Not TPA Ameliorates a Cellular Response of Cardiomyocytes To Anoxia and Reoxygenation," *Can. J. Cardiol.* 7(Suppl. A):p. 80A, Abstract No. 72, 1991.

Primary Examiner—Robert A. Schwartzman
(74) Attorney, Agent, or Firm—Clark & Elbing LLP; Kristina Bieker-Brady

(57) ABSTRACT

There is disclosed novel peptides, fragments or analogues thereof and polynucleotides encoding the same, obtained from streptokinase suitable for use in the amelioration of cell death and methods related thereto.

19 Claims, 3 Drawing Sheets

IAGPEWLLDR PSVNNSQLVV SVAGTVGTN QDISLKFFEI DLTSRPAHGG
KTEQGLSPKS KPFATDSGAM SHKLEKADLL KAIQEQLIAN VHSNDDYFEV
IDFASDATIT DRNGKVYFAD KDGSVTLPTQ PVQEFLLSGH VRVRPYKEKP
IQNQAKSVDV EYTVQFTPLN PDDDFRPGLK LTKLLKTLAI GDTITSQELL
AQAQSILNKN HPGYTIYERD SSIVTHDNDI FRTILPMDQE FTYRVKNREQ
AYRINKKSGL NEEINNTDLI SLEYKYVLKK GEKPYDPFDR SHLKLFTIKY
VDVDTNELLK SEQLLTASER NLDFRDLYDP RDKAKLLYNN LDAFGIMDYT
LTGKVEDNHD DTNRIITVYM GKRPEGENAS YHAYDKDRY TEEEREVYSY
LRYTGTPIPD NPDDK (SEQ. ID. No. 12)

FIG. 3

SEQUENCE LISTING

<160> NUMBER OF SEQ ID NOS: 16

<210> SEQ ID NO 1
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 1

Ser Val Asp Val Glu Tyr
 1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 2

Tyr Val Asp Val Asp Thr
 1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 3

Thr Val Asp Val Glu Tyr
 1               5

<210> SEQ ID NO 4
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 4

Tyr Val Asp Val Asp Thr Asn Glu Leu Leu Lys
 1               5                  10

<210> SEQ ID NO 5
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 5

Ser Val Asp Val Glu Tyr Thr Val Gln Phe Thr Pro Leu Asn Pro Asp
 1               5                  10                  15

<210> SEQ ID NO 6
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 6

-continued

Ser Val Asp Val Glu Tyr Thr Gln Phe Thr Asp Phe Arg Gly Lys Leu
1               5                   10                  15

Thr Lys Leu Leu
            20

<210> SEQ ID NO 7
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 7

Ser Val Asp Val Glu Tyr Thr Val Gln Phe Thr Pro Leu Asn Pro Asp
1               5                   10                  15

Asp Asp Phe Arg Pro
            20

<210> SEQ ID NO 8
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 8

Tyr Val Asp Val Asp Thr Asn Glu Leu Leu Lys Ser Glu Gln Leu Leu
1               5                   10                  15

Thr Ala Ser Glu
            20

<210> SEQ ID NO 9
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 9

Asn Phe Leu Arg Gly Lys Leu Lys Leu Tyr Thr Gly Glu Ala Cys Arg
1               5                   10                  15

Thr Gly Asp Arg
            20

<210> SEQ ID NO 10
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 10

Arg Leu Ile Leu Asp Ser Arg Val Leu Glu Arg Tyr Leu Leu Glu Ala
1               5                   10                  15

Lys Glu Ala Glu
            20

<210> SEQ ID NO 11
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 11

```
Glu Val Thr Glu Glu Glu Thr Val Pro Leu Lys Thr Leu Glu Ala
 1               5                  10                  15

Met Ile Asp Glu
             20
```

<210> SEQ ID NO 12
<211> LENGTH: 413
<212> TYPE: PRT
<213> ORGANISM: Artificial Sequence
<220> FEATURE:
<223> OTHER INFORMATION: Synthetic polypeptide

<400> SEQUENCE: 12

```
Ile Ala Gly Pro Glu Trp Leu Leu Asp Arg Pro Ser Val Asn Asn Ser
 1               5                  10                  15

Gln Leu Val Val Ser Val Ala Gly Thr Val Gly Thr Asn Gln Asp Ile
             20                  25                  30

Ser Leu Lys Phe Phe Glu Ile Asp Leu Thr Ser Arg Pro Ala His Gly
             35                  40                  45

Gly Lys Thr Glu Gln Gly Leu Ser Pro Lys Ser Lys Pro Phe Ala Thr
 50                  55                  60

Asp Ser Gly Ala Met Ser His Lys Leu Glu Lys Ala Asp Leu Leu Lys
 65                  70                  75                  80

Ala Ile Gln Glu Gln Leu Ile Ala Asn Val His Ser Asn Asp Asp Tyr
                 85                  90                  95

Phe Glu Val Ile Asp Phe Ala Ser Asp Ala Thr Ile Thr Asp Arg Asn
                100                 105                 110

Gly Lys Val Tyr Phe Ala Asp Lys Asp Gly Ser Val Thr Leu Pro Thr
            115                 120                 125

Gln Pro Val Gln Glu Phe Leu Leu Ser Gly His Val Arg Val Arg Pro
130                 135                 140

Tyr Lys Glu Lys Pro Ile Gln Asn Gln Ala Lys Ser Val Asp Val Glu
145                 150                 155                 160

Tyr Thr Val Gln Phe Thr Pro Leu Asn Pro Asp Asp Phe Arg Pro
                165                 170                 175

Gly Leu Lys Leu Thr Lys Leu Leu Lys Thr Leu Ala Ile Gly Asp Thr
            180                 185                 190

Ile Thr Ser Gln Glu Leu Leu Ala Gln Ala Gln Ser Ile Leu Asn Lys
            195                 200                 205

Asn His Pro Gly Tyr Thr Ile Tyr Glu Arg Asp Ser Ser Ile Val Thr
    210                 215                 220

His Asp Asn Asp Ile Phe Arg Thr Ile Leu Pro Met Asp Gln Glu Phe
225                 230                 235                 240

Thr Tyr Arg Val Lys Asn Arg Glu Gln Ala Tyr Arg Ile Asn Lys Lys
                245                 250                 255

Ser Gly Leu Asn Glu Glu Ile Asn Asn Thr Asp Leu Ile Ser Leu Glu
            260                 265                 270

Tyr Lys Tyr Val Leu Lys Lys Gly Glu Lys Pro Tyr Asp Pro Phe Asp
            275                 280                 285

Arg Ser His Leu Lys Leu Phe Thr Ile Lys Tyr Val Asp Val Asp Thr
    290                 295                 300

Asn Glu Leu Leu Lys Ser Glu Gln Leu Leu Thr Ala Ser Glu Arg Asn
305                 310                 315                 320

Leu Asp Phe Arg Asp Leu Tyr Asp Pro Arg Asp Lys Ala Lys Leu Leu
                325                 330                 335
```

```
Tyr Asn Asn Leu Asp Ala Phe Gly Ile Met Asp Tyr Thr Leu Thr Gly
            340                 345                 350

Lys Val Glu Asp Asn His Asp Asp Thr Asn Arg Ile Ile Thr Val Tyr
        355                 360                 365

Met Gly Lys Arg Pro Glu Gly Glu Asn Ala Ser Tyr His Ala Tyr Asp
    370                 375                 380

Lys Asp Arg Tyr Thr Glu Glu Arg Glu Val Tyr Ser Tyr Leu Arg
385                 390                 395                 400

Tyr Thr Gly Thr Pro Ile Pro Asp Asn Pro Asp Lys
                405                 410
```

<210> SEQ ID NO 13
<211> LENGTH: 4
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 1
<223> OTHER INFORMATION: Xaa=Ser or Tyr

<400> SEQUENCE: 13

Xaa Val Asp Val
 1

<210> SEQ ID NO 14
<211> LENGTH: 4
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 4
<223> OTHER INFORMATION: Xaa=Glu or Asp

<400> SEQUENCE: 14

Val Asp Val Xaa
 1

<210> SEQ ID NO 15
<211> LENGTH: 5
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 1
<223> OTHER INFORMATION: Xaa=Ser or Tyr
<221> NAME/KEY: VARIANT
<222> LOCATION: 5
<223> OTHER INFORMATION: Xaa=Glu or Asp

<400> SEQUENCE: 15

Xaa Val Asp Val Xaa
 1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 4
<223> OTHER INFORMATION: Xaa=Glu or Asp
<221> NAME/KEY: VARIANT
<222> LOCATION: 5

```
-continued

<223> OTHER INFORMATION: Xaa=Tyr or Thr

<400> SEQUENCE: 16

Val Asp Val Xaa Xaa
 1               5
```

PEPTIDES AND THEIR USE TO AMELIORATE CELL DEATH

CROSS-REFERENCE TO RELATED APPLICATION

This application is a continuation-in-part of U.S. application Ser. No. 08/759,599, filed Dec. 5, 1996, U.S. Pat. No. 5,917,013, which application claims the benefit of provisional Application No. 60/008,233, filed Dec. 6, 1995, both of which are incorporated by reference in their entirety.

TECHNICAL FIELD

The present invention generally relates to novel compositions and methods for use thereof in the amelioration of cell death. More specifically, the present invention is directed to peptides obtained from streptokinase, as well as derivatives and analogs thereof, and their use in the amelioration of apoptosis and/or necrosis.

BACKGROUND OF THE INVENTION

Cell death occurs in both normal human development and in pathological conditions. Two kinds of cell death have been recognized: apoptosis and necrosis. Briefly, apoptosis, or programmed cell death, is a natural process that is triggered by specific biological events and proceeds by well-defined mechanisms. Apoptosis occurs by compaction and convolution of the nuclear chromatin into dense masses, fragmentation of the nucleus, and blebbing of the plasma membrane, ultimately resulting in cell death. Even though 50% of an organism's cells are experiencing some stage of apoptosis at any given time, the process is observable in only about 0.1% of those cells.

Necrosis, on the other hand, is easily observed. Necrosis results from severe or sudden insult, for example as a result of physical trauma, anoxia, hyperthermia or chemically induced damage. Briefly, necrosis is typified by early changes in the structure and function of the mitochondria. When the mitochondria are unable to provide energy to the cell, the cell can no longer maintain homeostasis. The plasma membrane then loses its ability to regulate osmotic pressure and the cell swells and bursts, spilling its contents into the surrounding tissue and provoking an inflammatory response. In cases of severe injury or bacterial infection, this response can result in additional tissue damage. Cell necrosis is associated with diseases that result from the acute interruption of blood flow to any organ of the body. For example, the interruption of blood flow to the heart, brain, or kidney may produce, by way of example, myocardial infarction, cerebral infarction, or renal infarction, respectively. Cell necrosis is also associated with the toxic effects of bacteria and chemicals and bacterial or viral infections of any organ in the body.

Apoptosis appears to be genetically regulated. However, apoptosis can be induced by exposing cells to radiation, heat, cytotoxic agents, and abnormal changes in cellular biology. The mitochondria may also be involved in apoptosis. Excessive cell death may result in crippling degenerative disorders, for example, the annihilation of vital $CD4^+$ T-lymphocytes in HIV infected patients; the elimination of neurons, and other cell types, following ischemia and reperfusion; and the destruction of cells after exposure to ionizing or ultraviolet radiation in the treatment of neoplastic disorders. These disorders are thought to stem from ectopically programmed cell death, e.g., metabolic or infective factors that induce the apoptosis. Too little cell death can result in proliferative disorders, such as neoplastic disorders or autoimmune disease when a particular immune cell lives beyond its appropriate life span.

One common trigger of apoptosis in the acquisition of these disorders is oxidative stress, which causes the production of free radicals. Free radicals are highly reactive molecular species which interact with a wide variety of naturally occurring cellular components. Exposure to free radical leads to cumulative damage to cellular components and, ultimately, to the tissue itself.

A variety of factors may increase the free radical concentration and oxidative stress, thereby rendering the warm-blooded animal susceptible to cell death and its associated disorders. Such factors include considerations of genetics, nutritional status, exposure to drug therapy, drug metabolism, disease, and environmental factors. A change in any one of these factors may result in a failure of the body's defensive mechanisms and lead to cell death. Cellular damage has been invoked as a possible etiology in the development of various degenerative disorders, including, by way of example, cardiovascular disease, autoimmune disorders, arthritis, cancer, pancreatitis, hepatoxicity, cataracts, macular degeneration, accelerated aging, Parkinson's disease, Alzheimer's disease, and the like.

The present invention discloses novel compositions and methods for the amelioration of cell death, and further provides other related advantages.

SUMMARY OF THE INVENTION

As noted above, the present invention provides compositions and methods for the amelioration of cell death due to necrosis or apoptosis. Within one aspect of the present invention peptides obtained from a streptokinase are provided (as well as fragments, derivatives, and analogues thereof), which are capable of ameliorating cell death.

Within a related aspect of the invention, isolated polynucleotide sequences are provided which encode the aforementioned peptide, or a fragment or analogue thereof. Within certain embodiments of the invention, the polynucleotide sequence may be operably linked to a promoter within an expression vector, in order to allow expression of the polynucleotide sequence. Also provided are host cells which contain such expression vectors.

Other aspects of the present invention provide pharmaceutical compositions, comprising a peptide obtained from a streptokinase (as well as fragments, derivatives, and analogues thereof), in a suitable pharmaceutical, physiological, or medicamentally acceptable excipient or diluent.

Within yet another aspect of the present invention, methods of ameliorating cell death are provided comprising the general step of treating a warm-blooded animal by administering a therapeutically effective amount of a compound, as described above, such that cell death is ameliorated. In this regard the compound may be either a peptide or peptide derivative, a peptide analog, or, a nucleic acid molecule which directs the expression of the peptide or peptide derivative. In one embodiment of this aspect, the warm-blooded animal is suffering from a disorder selected from the group consisting of neurodegenerative disorders, cardiovascular diseases, immune diseases, neoplastic disorders, inflammatory disorders, myelodegenerative disease, viral disease and degenerative diseases of any organ.

Neurodegenerative disorders include, by way of example, Parkinson's, Alzheimer's, Huntington's, cerebellar degeneration, and FALS.

Cardiovascular diseases include, by way of example, hypertensive heart disease, heart failure, atherosclerosis, myocardial infarction, congestive heart disease and myocardial reperfusion injury.

Immune diseases include, by way of example, autoimmune disease, AIDS/HIV, and immune deficiencies. Autoimmune diseases include, by way of example, rheumatoid arthritis, systemic lupus erythematosus, insulin-dependent diabetes mellitus, myasthenia gravis, glomerulonephritis, lupus, pernicious anemia, dermatomyositis, enythema nodosum, Sjögren's syndrome, temporal arteritis, Wegener's granulomatosis, antiphospholipid syndrome, and autoimmune polyarthritides.

Neoplastic disorders include, by way of example, leukemia, sarcomas, myelomas, carcinomas, neuromas, melanoma, cancers of the breast, brain, colon, cervix, or prostrate, Hodgkin's disease, and non-Hodgkin's lymphoma.

Inflammatory diseases include, by way of example, inflammatory joint disorders, arthritis, and inflammatory-induced cell damage to eye, brain, and other organs. Viral diseases include, by way of example, viral infections, such as hepatitis, retroviral infections, and viral encephalitis. Other disorders include macular degeneration, cataracts, pancreatitis, Crohn's disease, ulcerative colitis, and accelerated aging.

In another aspect of the present invention, the warm-blooded animal is suffering from an insult selected from the group consisting of physical trauma, anoxia, hyperthermia, chemically-induced damage, and radiation-induced damage.

In still yet another aspect of the present invention, the warm-blooded animal has been subjected to a procedure selected from the group consisting of bypass surgery, chemotherapy, and organ transplantation.

These and other aspects of the present invention will become evident upon reference to the following detailed description and attached drawings. In addition, various references are set forth below which describe in more detail certain procedures or compositions (e.g., plasmids, etc.), and are therefore incorporated by reference in their entirety as if each were explicitly incorporated herein.

BRIEF DESCRIPTION OF THE DRAWINGS

FIG. 3 is an amino acid sequence of one representative streptokinase as described in K. W. Jackson and J. Tang, Biochemistry 21:6620–6625, 1982. A=alanine; C=cysteine; D=aspartic acid; E=glutamic acid; F=phenylalanine; G=glycine; H=histidine; I=isoleucine; K=lysine; L=leucine; M=methionine; N=asparagine; P=proline; Q=glutarnine; R=arginine; S=serine; T=threonine; V=valine; W=tryptophan; Y=tyrosine.

DETAILED DESCRIPTION OF THE INVENTION

Figure 1:
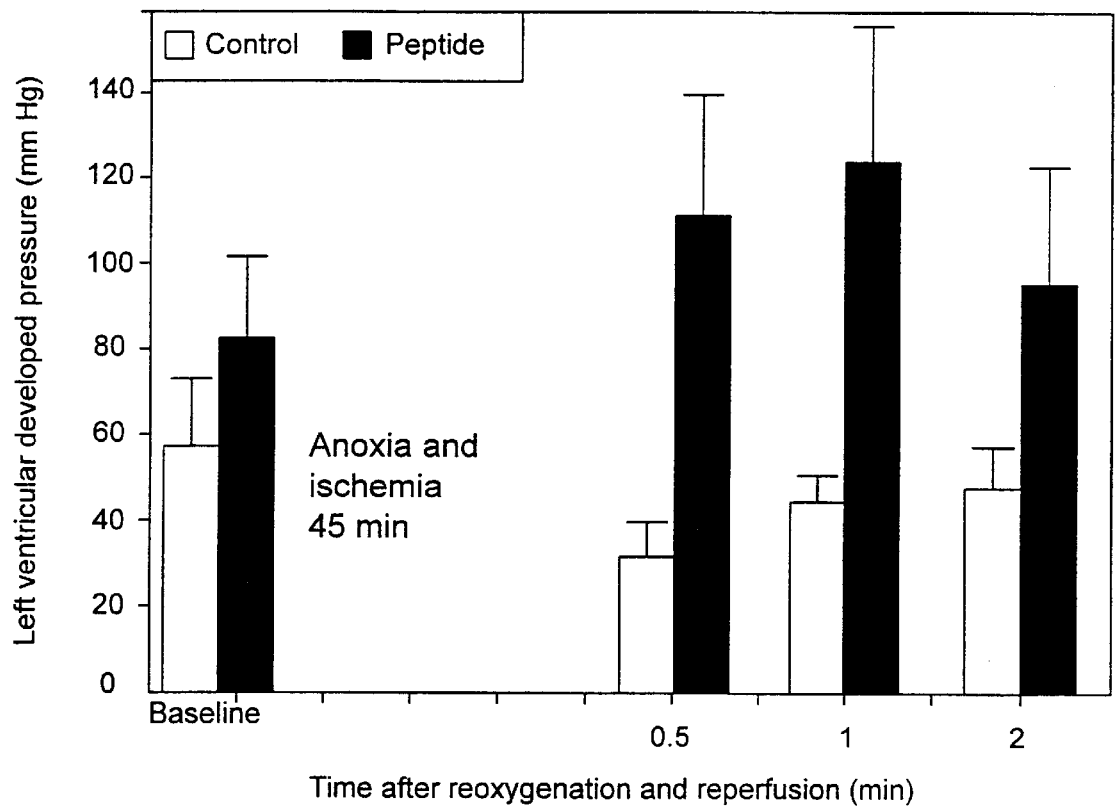
FIG. 1 is a bar graph which depicts left ventricular developed pressure, i.e., the difference between peak systolic pressure and resting left ventricular pressure, in the isolated rat heart that was exposed to 45 minutes of ischemia by subjecting the heart to an 80% reduction in perfusion flow rate, under anoxic conditions (85% $N_2$ and 5% $CO_2$), followed by reperfusion at 15 ml/min. and reoxygenation. There is a more rapid recovery in the hearts that received the peptide (20 mer) (SEQ. ID. No. 6) prior to reperfusion.

As noted above, the present invention generally relates to novel compositions and the use thereof in methods of ameliorating cell death. Specifically, the present invention pertains to novel peptides derived from a streptokinase and a method of use thereof to ameliorate apoptosis or necrosis.

Within the context of the present invention, the term "cell death" refers to apoptosis or necrosis. The term "apoptosis" refers to programmed cell death. The term "necrosis" refers to cell death as a response to overwhelming cellular or tissue injury. The term "ameliorate" or "amelioration" refers to an inhibition of cell death such that the incidence of cell death is generally decreased by 50%–80%, typically decreased by greater than 80% and, preferably, decreased by greater than 95%.

Peptides and Peptide Analogues

As noted above, the peptides of the present invention can be obtained or derived from a streptokinase (e.g., available from ICN, Inc., Costa Mesa, Calif., No. 101114) (FIG. 3) and identified by their ability to ameliorate cell death. In the context of the present invention, the term "streptokinase" includes any analogues, homologues, mutants, isomers, or derivatives, in addition to the naturally occurring molecule. The term "derived" refers to construction of a peptide based on the knowledge of a representative streptokinase sequence using any one of several suitable means, including, by way of example, isolation or synthesis.

Peptides of the present invention may be synthesized using any one of several means, including tea-bag methodology or solid phase peptide synthesis procedures described by Merrifield et al. (Biochemistry 21:5020–31, 1982), Houghten Wellings, D. A. (Proc. Nat'l. Acad. Sci. (USA) 82:5131–35, 1985); Atherton, E., Methods in Enzymology 289:44–66, 1997, or Guy, C. A.; Fields, G. B., Methods in Enzymology 289:67–83, 1997, or using a commercially available automated synthesizer, such as the Applied Biosystems 430 A Peptide Synthesizer.

Alternatively, suitable peptides may be isolated from streptokinase by digestion of the molecule using any suitable means including, by way of example, a protease including plasminogen, trypsin, urokinase, enterokinase, pepsin, papain, and staphylococcus aureus protease ("SAP"), or any combination thereof. Preferably, streptokinase is digested with plasminogen.

Suitable peptides prepared by either of the means described above may be purified using any one of several suitable means, including affinity columns, salt precipitations, anion/cation exchange columns, sizing columns, and gel electrophoresis based on size and charge. Preferably, purification is accomplished using reverse-phase high pressure liquid chromatography (HPLC).

Suitable peptides, prepared as described above, may be assayed using any one of several suitable means of identifying their ability to ameliorate cell death, including culturing three separate biological preparations: (1) and (2) are cultured for a period of time and under suitable conditions to induce apoptosis; and (3) is cultured as a control group. Apoptosis can be induced by any one of several means, including chemotherapeutic agents, hypoosmotic shock, ultraviolet radiation, gamma-radiation, soft beta-radiation, serum deprivation, or, specific receptor mediated or non-receptor mediated agents. Preferably, apoptosis is induced using ammonium persulfate which induces oxidative damage and, ultimately, results in cell death.

The peptide to be screened is administered to either biological preparation (1) or (2), and the percent cell death ascertained in all three biological preparations using, for example, trypan blue exclusion. The success of the peptide, for example, if added to biological preparation (1), can be gauged by comparison with the cell death in biological preparations (2) and (3). Generally, a 50%–80% decrease in cell death and, preferably, a greater than 80% decrease, over biological preparation (2), is the indicia of a successful peptide. Even more preferably, a greater than 95% decrease in cell death is the indicia of a successful peptide. Alternatively, a method such as that disclosed in WO 94/25621, may be suitable for screening the compounds of the present invention.

Suitable peptides may be analyzed by any one of several means to ascertain their composition, including, by way of example, amino acid analysis (e.g., R. L. Heinriksen and S. C. Meredith, *Anal. Biochem.* 160:65–74, 1984) after gas phase hydrolysis (N. M. Meltzer et al., *Anal. Biochem.* 160:356–61, 1987). The sequence of the streptokinase peptide may be confirmed by Edman degradation on a commercially available sequencer (e.g., R. M. Hewick et al., *J. Biol. Chem.* 15:7990–8005, 1981). Mass Spectral techniques can also be utilized for sequencing peptides and peptide libraries (see e.g., Brünjes, J.; Metzger, J. W.; Jung, G. in "Combinatorial Peptide and Nonpeptide Libraries", G. Jung Ed., VCH publishing, New York 1996, chapter 18, pp 511–521).

In a preferred embodiment of the present invention, suitable peptides may have the following core amino acid sequences: VAL-ASP-VAL (including— SER/TYR-VAL-ASP-VAL- (SEQ. ID. No. 13); -VAL-ASP-VAL-GLU/ASP- (SEQ. ID. No. 14); -SER/TYR-VAL-ASP-VAL-GLU/ASP- (SEQ. ID. No. 15); and -VAL-ASP-VAL-GLU/ASP-TYR/THR- (SEQ. ID. No. 16)).

Particularly preferred peptides in this regard include the following amino acid sequences:

a. SER-VAL-ASP-VAL-GLU-TYR (SEQ. ID. No. 1)

b. TYR-VAL-ASP-VAL-ASP-THR (SEQ. ID. No. 2)

c. THR-VAL-ASP-VAL-GLU-TYR (SEQ. ID. No. 3)

d. TYR-VAL-ASP-VAL-ASP-THR-ASN-GLU-LEU-LEU-LYS (SEQ. ID. No. 4)

e. SER-VAL-ASP-VAL-GLU-TYR-THR-VAL-GLN-PHE-THR-PRO-LEU-ASN-PRO-ASP-ASP-ASP (SEQ. ID. No. 5)

f. SER-VAL-ASP-VAL-GLU-TYR-THR-GLN-PHE-THR-ASP-PHE-ARG-GLY-LYS-LEU-THR-LYS-LEU-LEU (SEQ. ID. No. 6)

g. SER-VAL-ASP-VAL-GLU-TYR-THR-VAL-GLN-PHE-THR-PRO-LEU-ASN-PRO-ASP-ASP-ASP-PHE-ARG-PRO (SEQ. ID. No. 7)

h. TYR-VAL-ASP-VAL-ASP-THR-ASN-GLU-LEU-LEU-LYS-SER-GLU-GLN-LEU-LEU-THR-ALA-SER-GLU (SEQ. ID. No. 8)

In the context of the present invention, the term "peptide" includes analogues and fragments thereof. The term "analogue" refers to any derivative of the peptide and peptides in which one or more amino acids have been replaced with amino acids of similar size and charge, e.g., interchanging LEU and ILE or the attachment of another structure such as a cyclic compound or other molecule to the "peptide." Analogues also include peptides which contain one or more amino acids in an altered configuration (i.e., R or S; or, L or D). The term "fragment" refers to any fragment of the peptide which is capable of ameliorating cell death as described above. Preferably, fragments are at least four amino acids in length; even more preferably, fragments are at least six amino acids in length (see eg., SEQ I.D. Nos. 13, 14, 15 and 16).

Peptides of the present invention may also be modified in order to improve potency, bioavailability, and/or efficacy. For example, within one embodiment of the invention D-amino acid peptides, or retroenantio peptide sequences may be generated in order to improve the bioactivity and chemical stability of a peptide structure (see, e.g., Juvvadi et al., *J. Am. Chem. Soc.* 118, 8989–8997, 1996; Freidinger et al., *Science,* 210, 656, 1980).

Lactam constraints (see Freidinger, supra), and/or azabicycloalkane amino acids as dipeptide surrogates can also be utilized to improve the biological and pharmacological properties of the native peptides (see, e.g., Hanessian et al., "Design and Synthesis of Conformationally Constrained Amino Acids as Versatile Scaffolds and Peptide Mimetics," *Tetrahedron* 53:12789–12854, 1997).

Amide bond surrogates, such as thioamides (see Artis, D. R.; Lipton, M. A., *J. Am. Chem. Soc.* 120:12200, 1998), secondary and tertiary amines, heterocycles see, for example, (a) Zabrocki, J.; Dunbar, J. B.; Marshall, K. W.; Toth, M. V.; Marshall, G. R., *J. Org. Chem.* 57:202, 1992; (b) Garofolo, A.; Tarnus, C.; Remy, J.-M.; Leppik, R.; Piriou, F.; Harris, B.; Pelton, J. T. In *Peptides: Chemistry, Structure and Biology,* J. E. Rivier and G. R. Marshall, Editors; ESCOM Science Publishers B. V.: Leiden, *The Netherlands,* 833–834, 1990; (c) Beusen, D. D.; Zabrocki, J.; Slomczynska, U.; Head, R. D.; Kao, J. L.-F.; Marshall, G. R., *Biopolymers* 36:181, 1995; (d) Abell, A. D.; Hoult, D. A.; Jamieson, E. J., *Tetrahedron Lett.* 33:5831, 1992), olefin (see for example: Andres, C. J.; Macdonald, T. L.; Ocain, T. D.; Longhi, D. *J. Org. Chem.* 58:6609, 1993) and floroolefin replacements (see for example: (a) Boros, L. G.; De Corte, B.; Gimi, R. H.; Welch, J. T.; Wu, Y.; Handschumacher, R. E., *Tetrahedron Lett.* 35:6033, 1994; (b) Welch, J. T.; L in, *J. Tetrahedron* 52:291, 1996), among others (see review in Spatola, A. F. in "Chemistry and Biochemistry of Amino Acids, Peptides and Proteins" Wenstein, B. Ed. Marcel Dekker, New York, 1983 Vol. 7, pp 267–357) can also be utilized to prevent enzymatic degradation of the peptide backbone (thereby resulting in improved activity).

Replacement of the aromatic amino acids such as Phe and Tyr by constrained aromatic amino acid analogs can also be utilized to restrict the geometry of the aromatic ring and thereby improve receptor affinity. Examples of syntheses of the constrained aromatic amino acid analogs as well as lead references for their use in studying peptide structures can be found in: (a) Gibson (née Thomas), S. E.; Guillo, N.; Middleton, R. J.; Thuilliez, A.; Tozer, M. J. *J. Chem. Soc., Perkin Trans.* 1:447, 1997; (b) Collot, V.; Schmitt, M.; Marwah, A. K.; Norberg, B.; Bourguignon, J.-J. *Tetrahedron Lett.* 38:8033, 1997; (c) Kazmierski, W. M.; Urbanczyk-Lipkowska, Z.; Hruby, V. J. *J. Org. Chem.* 59:1789, 1994; (d) Cativiela, C.; Diaz-de-Villegas, M. D.; Avenoza, A.; Peregrina, J. M. *Tetrahedron* 49:10987, 1993; (e) de Laszlo, S. E.; Bush, B. L.; Doyle, J. J.; Greenlee, W. J.; Hangauer, D. G.; Halgren, T. A.; Lynch, R. J.; Schorn, T. W.; Siegl, P. K. S. *J. Med. Chem.* 35:833, 1992; (f) Seebach, D.; Boes, M.; Naef, R.; Schweizer, W. B. *J. Am. Chem. Soc.* 105:5390, 1983; (g) Chung, J. Y. L.; Wasicak, J. T.; Arnold, W. A.; May, C. S.; Nadzan, A. M.; Holladay, M. W. *J. Org. Chem.* 55:270, 1990; (h) Herdeis, C.; Hubmann, H. P.; Lotter, H. *Tetrahedron: Asym.* 5:351, 1994; (i) Belokon', Y. N.; Bulychev, A. G.; Pavlov, V. A.; Fedorova, E. B.; Tsyryapkin, V. A.; Bakhmutov, V. A.; Belikov, V. M. *J. Chem. Soc.,*

*Perkin Trans.* 1:2075, 1988; (3) Sarges, R.; Tretter, J. R., *J. Org. Chem.* 39:1710, 1974; (k) Semple, J. E.; Minami, N. K.; Tamura, S. Y.; Brunck, T. K.; Nutt, R. F.; Ripka, W. C., *Bioorg. Med. Chem. Lett.* 7:2421, 1997; (l) Pastó, M.; Moyano, A.; Pericàs, M. A.; Riera, A., *J. Org. Chem.* 62: 8425, 1997; (m) Kühn, C.; Lindeberg, G.; Gogoll, A.; Hallberg, A.; Schmidt, B. *Tetrahedron* 53:12497, 1997; (n) Liao, S.; Shenderovich, M. D.; Lin, J.; Hruby, V. J., *Tetrahedron* 53:16645, 1997; (o) Van Betsbrugge, J.; Van Den Nest, W.; Verheyden, P.; Tourwé, D., *Tetrahedron* 54:1753, 1998.

Conversion of linear peptides to cyclic peptide analogs can also be utilized to improve metabolic stability, since cyclic peptides are much less sensitive to enzymatic degradation (see generally, Veber, et al. *Nature* 292:55–58, 1981).

Yet other peptide analogues may be generated based upon the presence of many valine residues in some of the peptide sequences described herein. Within one embodiment, peptide sequences possessing constrained valine analogs such as a proline-valine chimera (see generally Sharma and Lubell, "Regioselective Enolization and Alkylation of 4-Oxo-N-(9-phenylfluoren-9-yl)proline: Synthesis of Enantiopure Proline-Valine and Hydroxyproline-Valine Chimeras," *J. Org. Chem.* 61:202–209, 1996), can be generated.

Similarly, amino acid chimeras that contain proline analogues possessing the characteristics of other amino acids can be generated for studying the spatial requirements for receptor affinity and biological activity of peptides. Such analogs would be particularly useful for modifing the Asp and Glu residues of the active peptides.

Furthermore, α-alkyl branched amino acids (see: Toniolo, C.; Benedetti, E., *Macromolecules* 24:4004, 1991; and references therein.), dehydro amino acids (see for example: Dehydro-Enkephalins IV. Discriminative Recognition of Delta and Mu Opiate Receptors by Enkephalin Analogs. Y. Shimohigashi, C. H. Stammer, T. Costa et al., *Biochem. Biophys. Res. Commun.* 104:583–590, 1982) as well as cyclopropane amino acid analogs (reviewed in: C. H. Stammer *Tetrahedron* 46:2231–2254, 1990) can be introduced into peptides in order to induce local conformational constraint that can enhance activity by restricting the back-bone and side-chain geometry of the native peptide.

Peptides can also be modified in order to improve absorption (see generally, Annual Reviews of Medicinal Chemistry), including for example, addition of sugar residues to enhance transport across the blood-brain barrier.

Peptides can also be modified utilizing end group capping as esters and amides in order to slow or prevent metabolism and enhance lipophilicity. Dimers of the peptide attached by various linkers may also enhance activity and specificity (see for example: Y. Shimohigashi et al., "Enkephalin Dimers and Their Handicapped Analogs as Probes for Elucidation of Ligand-Opiate Receptor Interaction," in *Peptide Chemistry* 1988, Proceedings of the 26th Symposium on Peptide Chemistry, Tokyo, October 24–26, pgs. 47–50, 1989).

Other peptide modifications suitable for use within the present invention include the addition to either or both ends of each peptide, or to the VAV sequence, D-penicillamine, or —NH$_2$, cyclization of the peptide, linkage of two or more peptides via a bridge (e.g., utilizing hydrazide), halogenation of peptide sequences, addition of Phe residues, and conjugation with other moieties, such as a methyldihydropyridine.

Peptide analogues can also be generated and selected from combinatorial libraries. Representative examples of suitable techniques are described in more detail in U.S. Pat. Nos. 4,528,266 and 4,359,535, and Patent Cooperation Treaty Publication Nos. WO 92/15679, WO 92/15677, WO 90/07862, WO 90/02809, or purchased from commercially available sources (e.g., New England Biolabs Ph.D.™ Phage Display Peptide Library Kit).

Expression of Peptides

Another aspect of the present invention provides polynucleotides which encode the above described peptides, analogues or fragments thereof. Polynucleotides and analogues thereof include, by way of example, RNA, DNA analogues thereof, including chimerics and PNA. The polynucleotides of the present invention may be synthesized or isolated. Synthesis may be accomplished using any one of several means including standard polynucleotide synthesis procedures. The polynucleotides coding for the aforementioned peptides could either be inserted into a standard plasmid or viral vector, introduced into bacterial or eukaryotic cells and the peptides of the present invention expressed and isolated.

Expression of the inserted polynucleotide can be determined in vitro using any one of the techniques described above. Expression of the inserted polynucleotide can be determined in vivo using any one of several methods, including, by way of example, immunofluorescence using a fluoresceinated ligand.

The sequences, constructs, vectors and other materials comprising the present invention can advantageously be in the enriched or isolated form. Within the context of the present invention, "enriched" means that the concentration of the material is at least about 2, 3, 4, 10, 100, or 1000 times its natural concentration, for example, advantageously 0.01% by weight, preferably at least about 0.1% by weight. Enriched preparations of about 0.5%, 1%, 5%, 10%, and 20%, by weight, are also contemplated.

Within the context of the present invention, the term "isolated" requires that the material be removed from its original environment (e.g., the natural environment if it is naturally occurring). For example, a naturally occurring oligonucleotide or peptide present in a living animal is not "isolated," but the same oligonucleotide or peptide, separated from some or all of the coexisting materials in the natural system, is "isolated." Within one embodiment, when the term "purified" is utilized in the context of peptides, this means that, upon application of the peptide to SDS-PAGE analysis, followed by Coomassie blue staining, a single band is visible on the gel.

Another aspect of the present invention provides constructs including one or more of the polynucleotides, as broadly described above. The constructs comprise a vector, such as a plasmid or viral expression vector, into which a polynucleotide of the present invention has been inserted, in either a sense or antisense orientation. Preferably, the construct further contains regulatory regions, including, for example, a promoter, operably linked to the polynucleotide. Large numbers of suitable vectors and promoters are known and are commercially available. The following expression vectors are provided by way of example: Prokarvotic: pBC, pBluescript SK, pBK, pNH8a, pNH16a, pNH18a, pNH46a, pCR-SCRIPT (Stratagene), ptrc99A, pKK223-3, pKK233-3, pDR540, pRIT5 (Pharmacia). Eukarvotic: TBK, pSV2cat, pOG44, pOG45, pXT1, pMC1neo, pMC1neo Poly A, pSG, pSG5 (Stratagene), pSVK3, pBPV, pMSG, pSVL (Pharmacia). Viral: retroviral, adenoviral, phage-based vectors, and vaccinia virus.

Promoter regions may be selected from any desired gene using chloramphenicol transferase ("CAT") vectors or other vectors with selectable markers. Two appropriate vectors are pKK232-8 and pCM7. Particular named bacterial promoters include lacI, lacZ, T3, T7, gpt, lambda $P_{RO}$ and trc. Eukaryotic promoters include CMV immediate early, HSV thymidine kinase, early and late SV40, LTRs from retrovirus and mouse metallothionein-I. Selection of the appropriate vector and promoter is well within the level of one of ordinary skill in the art.

In a further embodiment, the present invention provides host cells containing the above-described construct. The host cell can be a eukaryotic cell, for example, a mammalian cell or a yeast cell; or a prokaryotic cell, such as a bacterial cell. Introduction of the construct into the host cell can be affected using any one of several methods known in the art, including by calcium phosphate transfection, DEAE, dextran mediated transfection, infection, or electroporation, as described in detail in, e.g., Davis et al., *Basic Methods of Molecular Biology*, 1986.

Constructs in host cells can be used in a conventional manner to produce the peptides coded by the polynucleotides, as described above, or the host cells can be administered directly to an animal in need thereof, as described below. Alternatively, the encoded peptide can be synthetically produced by conventional peptide synthesizers.

Gene Therapy

A wide variety of gene delivery vectors may be utilized to deliver and/or express a desired peptide of interest in host cells. For example, within one aspect of the present invention, retroviral gene delivery vehicles may be utilized. Briefly, retroviral gene delivery vehicles of the present invention may be readily constructed from a wide variety of retroviruses, including for example, B, C, and D type retroviruses as well as spumaviruses and lentiviruses (see RNA Tumor Viruses, Second Edition, Cold Spring Harbor Laboratory, 1985). Such retroviruses may be readily obtained from depositories or collections such as the American Type Culture Collection ("ATCC"; Rockville, Md.), or isolated from known sources using commonly available techniques. Representative examples of retroviral gene delivery vectors are described in more detail in EP 0,415,731; PCT Publication Nos. WO 90/07936; WO 91/0285, WO 9311230; WO 9310218, WO 9403622; WO 9325698; WO 9325234; and U.S. Pat. Nos. 5,219,740, 5,716,613, 5,851,529, 5,591,624, 5,716,826, 5,716,832, and 5,817,491.

Other suitable gene delivery vectors can be generated from alphaviruses (see e.g., U.S. Pat. Nos. 5,091,309 and 5,217,879, 5,843,723, and 5,789,245), recombinant adenoviral vectors (see e.g., U.S. Pat. No. 5,872,005), and numerous other viruses such as pox viruses, such as canary pox virus or vaccinia virus (Fisher-Hoch et al., *PNAS* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112, 4,769,330 and 5,017,487; WO 89/01973); SV40 (Mulligan et al., *Nature* 277:108–114, 1979); influenza virus (Luytjes et al., *Cell* 59:1107–1113, 1989; McMicheal et al., *N. Eng. J. Med.* 309:13–17, 1983; and Yap et al., *Nature* 273:238–239, 1978); herpes (Kit, *Adv. Exp. Med. Biol.* 215:219–236, 1989; U.S. Pat. No. 5,288, 641); HIV (Poznansky, *J. Virol.* 65:532–536, 1991); measles (EP 0 440,219); Semliki Forest Virus, and coronavirus, as well as other viral systems (e.g., EP 0,440,219; WO 92/06693; U.S. Pat. No. 5,166,057).

In addition to the above viral-based vectors, numerous non-viral gene delivery vehicles may likewise be utilized within the context of the present invention. Representative examples of such gene delivery vehicles include direct delivery of nucleic acid expression vectors or naked DNA alone (see e.g., U.S. Pat. Nos. 5,814,482 and 5,580,859), polycation condensed DNA linked or unlinked to killed adenovirus (Curiel et al., *Hum. Gene Ther.* 3:147–154, 1992), DNA ligand linked to a ligand (Wu et al., *J. of Biol. Chem.* 264:16985–16987, 1989), and nucleic acid containing liposomes (e.g., WO 95/24929 and WO 95/12387).

Pharmaceutical Compositions, and Methods of Treatment

Pharmaceutical compositions containing the peptide, fragments or analogues thereof, or associated polynucleotides and constructs thereof (hereinafter referred to as "the compounds of the present inventions") in an admixture with a pharmaceutical carrier or diluent can be prepared according to conventional pharmaceutical compounding techniques. Administration should account for the possibility of degradation of compounds of the present invention. The carrier may take a wide variety of forms depending on the form of preparation desired for administration, e.g., intravenous, intradermal, intraperitoneal, intramuscular, nasal, oral, topical, aerosol, suppository, parenteral or spinal injection. Preferably, the peptide is administered directly to the targeted site, i.e., by stereotactic injection or other suitable means.

Pharmaceutical composition containing the peptide, fragment or analogues thereof or polynucleotides and constructs thereof may be combined with agent or drug that inhibits or delays or retards the metabolism/degradation of the peptide, fragments or analogues.

If necessary, the pharmaceutical preparations can be subjected to conventional pharmaceutical adjuvants such as preserving agents, stabilizing agents, wetting agents, salts for varying the osmotic pressure, and the like. The present pharmaceutical preparations may also contain other therapeutically valuable substances.

Within this embodiment of the present invention, the compounds of the present invention may be delivered using a suitable liposome delivery system, including, by way of example, those described in U.S. Pat. No. 4,241,046; 4,235, 871; 4,394,448; 4,483,929; 4,745,074; 4,766,046; 4,873, 088; 5,077,057; 5,180,713; and 5,277,914; or in Rahman et al., *J. of Liposome Research* 4:167–192, 1994.

Compounds of the present invention may also be delivered by chronic infusion using any suitable method known in the art, including an osmotic minipump (Alza Corp.) or delivery through a time release or sustained release medium. Suitable time release or sustained release systems include any methods known in the art, including media such as Elvax (or see, for example, U.S. Pat. Nos. 5,015,479, 4,088,798, 4,178,361, and 4,145,408). When using chronic infusion, time release, or sustained release mechanisms, the composition may be stereotactically injected, orally, parenterally, or intramuscularly administered.

When polynucleotides of the present invention or constructs thereof are transfected or infected into a mammalian host cell, the mammalian cells may be administered to the patient in need thereof by any method known in the art, including that outlined in U.S. Pat. No. 5,082,670 (see also the gene therapy discussion provided above).

In another aspect of the present invention, the compositions of the present invention are utilized to treat diseases and conditions related to aging, cellular differentiation, and physical insult. These conditions and diseases include, by way of example, infectious diseases (e.g., viral, bacteria, parasite, or, prion-based diseases), degenerative disorders, immune disorders, aging, cardiovascular disorders, and neoplastic disorders.

In one embodiment of this aspect of the present invention, compositions of the present invention (as described above) are administered to treat or prevent a warm-blooded animal suffering from or susceptible to a viral disease. The association of cell death with a particular viral disorder may be determined by standard means. Such viral diseases include, by way of example, hepatitis, retroviral infections, and viral encephalitis, and AIDS/HIV (Fauci, A. S., *Science* 262:1011, 1993; Ameisen, J. C., *Immunol. Today* 13:388, 1992; Gorla, R. et al., *AIDS Research and Human Retroviruses* 10(9):1097).

Compounds of the present invention may also be administered to treat a warm-blooded animal suffering from, or susceptible to, a neurodegenerative disorder. The association of cell death with a particular neurodegenerative disorder may be determined by establishing, for example, indicators of defects of neurologic function. Such neurodegenerative disorders include, by way of example, Parkinson's disease, (Beal, M. F. et al., *TINS* 16(4):125, 1993; Bloem, B. R. et al., *J. Neurol. Sci.* 97:293 1990; Brennan, W. A. et al., *J. Neurochem.* 44:1948, 1985); Alzheimer's disease, (Beal, M. F. et al., *TINS* 16(4):125, 1993, Beal, M. F., *Ann. Neurol.* 31:119, 1992); Huntington's disease, (Beal, M. F. et al. *TINS* 16(4):125, 1993; Bloem, B. R. et al., *J. Neurol. Sci.* 97:293 1990; Brennan, W. A. et al., *J. Neurochem.* 44:1948, 1985); cerebellar degenerations, (Beal, M. F. et al., *TINS* 16(4):125, 1993); and, familial amyotrophic lateral sclerosis (FALS) (Olanow, C. W., *TINS* 16:439, 1993).

Compounds of the present invention may also be administered to treat or prevent a warm-blooded animal suffering from, or susceptible to, a cardiovascular disease. The association of cell death with a particular cardiovascular disease may be determined by any suitable means including microscopy of trypan blue exclusion, histologic examination for necrosis, or, DNA fragmentation assays (see Fliss and Gattinger, 1996, infra). Such cardiovascular diseases include, by way of example, atherosclerosis, myocardial infarction, heart failure, cardiomyopathy, myocardial reperfusion injury, and hypertensive heart disease. Assessment of the suitability of peptides, or peptide analogues in the treatment of coronary disease may be accomplished, for example, utilizing the rat model of ligation/reperfiusion (see generally, Fliss and Gattinger, *Cir. Res.* 79:949–956, 1996).

Compounds of the present invention may also be administered to treat a warm-blooded animal suffering from, or susceptible to, autoimmune disease. The association of cell death with a particular autoimmune disorder may be determined, for example, by biochemical tests such as antibodies to virus or anti-DNA antibodies, microscopic appearance of blood cells and histologic appearance of affected tissue. Such immune diseases include, by way of example, AIDS/HIV, autoimmune disease and immune deficiencies. Autoimmune diseases include rheumatoid arthritis, systemic lupus erythematosus, insulin-dependent diabetes mellitus, lupus, pernicious anemia, dermatomyositis, enythema nodosum, Sjögren's syndrome, temporal arteritis, myasthenia gravis, Wegener's granulomatosis, glomerulonepliritis, anti-phospholipid syndrome, and autoimmune polyarthritides. The connection between apoptosis and autoimmune disease has been documented in WO 94/08454.

Compounds of the present invention may also be administered to treat a warm-blooded animal suffering from, or susceptible to, a neoplastic disorder. The association of cell death with a particular neoplastic disorder may be determined by, for example, microscopic examination of blood elements, histologic appearance of tissue, and genetic testing of tissue and blood-formed elements. Such neoplastic disorders include, by way of example, leukemia, sarcomas, myelomas, carcinomas, neuromas, melanoma, cancers of the breast, brain, colon, cervix, and prostrate, Hodgkin's disease, and non-Hodgkin's lymphoma.

Compounds of the present invention may also be administered to treat a warm-blooded animal suffering from, or susceptible to, an inflammatory disorder. The association of cell death with a particular inflammatory disorder may be determined by, for example, x-ray examination, blood tests such as, but not restricted to, rheumatoid factor and histologic appearance of tissue. Such inflammatory disorders include, by way of example, inflammatory joint disorders such as arthritis and inflammatory induced cell damage to the eye, brain, and other organs.

Compounds of the present invention may also be administered to treat a warm-blooded animal which has been subjected to physical insult. The term "physical insult" refers to injury resulting from sudden or severe shock, for example, from physical trauma, anoxia, hyperthermnia, hypothermia, chemically induced damage, and acute tissue injury such as trauma to the brain, spinal cord, kidney, heart, lungs, liver, skin and any other organ of the body.

Compounds of the present invention may also be administered to treat a warm-blooded animal suffering from such conditions as ischemia or reperfiusion injury of various body organs, including, but not limited to, myocardial ischemia and reperfusion injury, renal ischemia, brain ischemia and/or reperfusion injury, spinal cord ischemia or reperfusion injury, retinal ischemia or infaction, and stroke.

Compounds of the present invention may also be administered to treat a warm-blooded animal suffering from such toxic insult as liver toxicity, pulmonary toxicity, and toxic damage to other body organs from chemicals, radiation and other noxious substances.

Compounds of the present invention may also be administered to treat a warm-blooded animal suffering from such conditions as macular degeneration, cataract formation, pancreatitis, CrohI's disease, ulcerative colitis and accelerated aging.

Compounds of the present invention may also be administered to treat a warm-blooded animal suffering from spinal cord disease, such as motor neuron diseases, degeneration of spinal cord, Guillan Bare Syndrome, and demyelinating disease.

Compounds of the present invention may also be administered to treat a warm-blooded animal which has been subjected to a procedure with which cell death is associated. Such procedures include, by way of example, cardiac catherization, bypass surgery, chemotherapy, and chemically-induced reperfusion. This association is determined by clinical examination and appropriate testing, depending on the organ. By way of example, such tests include, echocardiograms, electrocardiograms, nuclear studies, and biochemical tests, e.g., CK, and CK-MB.

Compounds of the present invention may also be administered to treat a warm-blooded animal which has been administered therapeutics which subject the animal to oxidative stress. The free radical production associated with oxidative stress may be identified and evaluated to ascertain the effect of the therapeutics using any suitable method, including thiobarbaturic acid, colormetric assays (TBARS), and spin resonance. Such therapeutics include, by way of example, clozapine, AZT, and anthracyclines.

Compounds of the present invention may also be administered to a biological preparation. In the context of the present invention, the term "biological preparation" refers to an ex vivo cell culture.

The compounds of the present invention or any combination thereof are administered in a therapeutically effective amount. A therapeutically effective amount is that amount sufficient to reduce cell death. A therapeutically effective amount can be determined by in vitro experiment followed by in vivo studies. The optimal dosage is that which produces maximal improvement with tolerated side effects. The optimal dosage is determined empirically and balances the benefits and adverse side effects.

The term "treatment" as used within the context of the present invention, refers to reducing or alleviating symptoms in a subject, preventing symptoms from worsening or progressing, inhibition or elimination of the causative agent, or prevention of the infection or disorder in a subject who is free therefrom. Thus, for example, treatment of infection includes destruction of the infecting agent, inhibition of or interference with its growth or maturation, neutralization of its pathological effects and the like. An unbalanced state disorder is "treated" by partially or wholly remedying the imbalance which causes the disorder or which makes it more severe. Representative examples of warm-blooded animals that may be "treated" include humans, horses, cows, pigs, sheep, dogs, cats, rats and mice.

A disorder is "treated" by partially or wholly remedying the deficiency which causes the disorder or which makes it more severe. For example, a disorder such as myocardial infarction is considered to be treated if administration of the composition provided herein (i) improves survival, (ii) results in fewer morbid events from the complications of myocardial infarction (e.g., heart failure and arrhythmias), or (iii) there is evidence of a lesser amount of damage to the heart due to a myocardial infarction (e.g., as assessed by the release of creatine kinase or imaging of the heart).

The following examples are provided by way of illustration, and not by way of limitation.

EXAMPLES

Example 1

Amelioration of Cell Death in Cardiac Myocytes

This example serves to demonstrate an assay useful to test peptides for their ability to ameliorate cell death.

Cardiac myocytes from embryonic chick hearts were grown in culture using the procedures described in Rabkin, *Exper. Cell. Res.* 188:262–266, 1990. Briefly, white Leghorn eggs were incubated in an automatic incubator (March Rollex, Calif., USA) for 7 days at 37.8° C. and 87% humidity. Hearts were then isolated under sterile conditions from the 7-day chick embryo. Blood and connective tissue were removed under a dissecting microscope in a solution of balanced salts (DMS8) with the following composition (mM): NaCl 116, KCl 5.4, $NaH_2PO_4$ 1 and dextrose 5.6. Disaggregation was carried out by 5-minute digestions in 0.005% trypsin (Gibco Laboratories, Burlington, Ontario), 0.1% BSA and $1 \times 10^7$ DNAse per mL, DMS8 (Worthington Biochemicals, Frederic, N.J., USA) at 37° C. After three digestions, the digests were diluted 1:5 in culture medium and the cells centrifuged for three minutes at 1000 g and plated.

The cultured cardiac myocytes were incubated with 1 mM ammonium persulfate for 2 hours at 37° C. to induce oxidative damage. Cell viability was assessed by Trypan blue exclusion. Six samples containing cells were then incubated with 0.0, 0.000375, 0.00375, 0.0375, 0.375 and 37.5 μM streptokinase (Hoechts-Roussel Pharmaceuticals), respectively, and 0.0, 0.000246, 0.00246, 0.0246, 0.246 and 24.6 μM plasminogen, respectively (see Table 1), for 1–2 hours at 37° C. and assessed by Trypan blue exclusion.

Control cell samples were treated with 1 mM ammonium persulfate in the absence of streptokinase (STK) and plasminogen under the same conditions.

The results are described in Table 1 in terms of the percent cell death induced by ammonium persulfate. The data represents the mean of six (6) duplicate determinations, none of which differed by more than 5%.

TABLE 1

| Streptokinase (μM) | Plasminogen (μM) | Cell Death (%) |
|---|---|---|
| 0 (Control) | 0 (Control) | 81 |
| 0.000375 | 0.000246 | 50 |
| 0.00375 | 0.00246 | 37 |
| 0.0375 | 0.0246 | 29 |
| 0.375 | 0.246 | 25 |
| 37.5 | 24.6 | 16 |

Example 2

Separation of Streptokinase Fragments by Reverse Phase HPLC

This example serves to demonstrate the isolation of peptides derived from streptokinase and their ability to ameliorate cell death in cardiac myocytes.

Streptokinase was incubated with plasminogen at a 1:1 molar concentration for 1–2 hours at 37° C. Streptokinase and plasminogen fragments were subsequently separated using a reverse phase phenyl HPLC column (Waters) and a linear gradient of 1%/min and an isopropanol gradient in 0.1 ammonium bicarbonate buffer, pH 6.5.

Each of the nineteen (19) resulting fractions was tested for the peptide's ability to ameliorate cell death according to the assay described in Example 1. The results of this assay are presented in Table 2. The data in Table 2 represent the mean of duplicate determinations. None of the determinations differed by more than 5%.

TABLE 2

| Fraction Number | Cell Death (%) |
|---|---|
| 1 | 87 |
| 2 | 79 |
| 3 | 79 |
| 4 | 62 |
| 5 | 83 |
| 6 | 77 |
| 7 | 81 |
| 8 | 79 |
| 9 | 82 |
| 10 | 63 |
| 11 | 78 |
| 12 | 29 |
| 13 | 39 |
| 14 | 80 |
| 15 | 76 |
| 16 | 63 |

TABLE 2-continued

| Fraction Number | Cell Death (%) |
| --- | --- |
| 17 | 79 |
| 18 | 74 |
| 19 | 77 |

The HPLC-purified peptides eluted in fractions 12 and 13 were analyzed by amino acid analysis (R. L. Heinriksen and S. C. Meredith, *Anal. Biochem.* 160:65–74, 1984) after gas phase sequencing (N. M. Meltzer et al., *Anal. Biochem.* 160:356–61, 1987). The seqence of the purified peptide was determined by Edman degradation on a commerically available seequencer (R. M. Hewick et al., *J. Biol. Chem.* 15:7990–8005, 1981). The sequences were:

fraction 12: YVDVDTNELLKSEQLLTASE (SEQ. ID NO. 8)

fraction 13: SVDVEYTVQFTPLNPDDDFRP (SEQ. ID NO. 7)

Example 3

Amelioration of Cell Death by Synthesized Peptides

This example serves to demonstrate the suitability of specific peptides in amelioration of cell death.

Based on the sequences identified in Example 2, peptides were synthesized using a commercially available automated synthesizer (Applied Biosystems 430 A Peptide Synthesizer), purified by and tested according to the assay described in Example 1 for their ability to ameliorate cell death in cardiac myocytes. The sequences for these peptides were:

6 mer #1: SVDVEY (SEQ. ID NO. 1)

6 mer #2: YVDVDT (SEQ. ID NO. 2)

6 mer #3: TVDVEY (SEQ. ID NO. 3)

11 mer: YVDVDTNELLK (SEQ. ID NO. 4)

18 mer: SVDVEYTVQFTPLNPDDD (SEQ. ID NO. 5)

20 mer: SVDVEYTQFTDFRGKLTKLL (SEQ. ID NO. 6)

fraction 12: YVDVDTNELLKSEQLLTASE (SEQ. ID NO. 8)

fraction 13: SVDVEYTVQFTPLNPDDDFRP (SEQ. ID NO. 7)

Irrelevant #1: NFLRGKLKLYTGEACRTGDR (SEQ. ID NO. 9)

Irrelevant#2: RLILDSRVLERYLLEAKEAE(SEQ.ID. NO. 10)

Irelevant #3: EVTEEEETVPLKThE-AMIDE (SEQ. ID NO. 11)

Table 3 presents the percentage of dead cells as measured by Trypan blue assessment as described in Example 1. The data in Table 3 represents means of duplicate determinations, which did not differ by more than 5%.

TABLE 3

| Peptide | Peptide Concentration ($\mu$M): | | | | |
| --- | --- | --- | --- | --- | --- |
|  | 0 | 5 | 10 | 15 | 20 |
| 20 mer | 80.3 | 47.6 | 35.4 | 31.6 | 23.1 |
| 6 mer #1 | 82.4 | 51.9 | — | — | 36.8 |
| 6 mer #2 | 82.4 | 37.0 | — | — | 25.4 |

TABLE 3-continued

| Peptide | Peptide Concentration ($\mu$M): | | | | |
| --- | --- | --- | --- | --- | --- |
|  | 0 | 5 | 10 | 15 | 20 |
| 6 mer #3 | — | — | — | — | — |
| 11 mer | 80.7 | 38.6 | — | — | 54.4 |
| 18 mer | 84.5 | — | — | — | 54.4 |
| Irrelevant #1 | 79.6 | 77.1 | — | — | 67.6 |
| Irrelevant #2 | 79.6 | 77.4 | — | — | 76.1 |
| Irrelevant #3 | 79.6 | 79.5 | — | — | 81.1 |

These peptides effectively protect cells against cell death in the low micromolar range and exhibit a good dose-response relationship. The highest concentration of the 20 mer peptide (SEQ. ID NO. 6) was able to reduce the number of dead cells to the 20% range, despite the presence of agents designed to induce cell death. This is comparable to cell death observed under control conditions (i.e., in the absence of ammonium persulfate). Three irrelevant peptides of different sequences, but approximately the same length, utilized as negative controls, did not show any significant effect on cell viability in this assay.

Example 4

Amelioration of Cell Death in Isolated Intact Rat Heart

This example serves to demonstrate the ability of the peptides of the present invention to ameliorate cell death in the heart.

Rats weighing between 0.3 and 0.4 kilograms were injected with heparin and then 1 hr. later killed by cervical fracture. Their hearts were immediately excised and placed in an oxygenated Krebs-Henseleit solution of the following composition (in millimole/liter): NaCl, 119.9; KCl, 6.0; NaHCO$_3$, 25.0; MgSO$_4$, 1.2; CaCl$_2$, 1.6; KH$_2$PO$_4$, 1.2; and glucose, 10.0. The aorta was cannulated and the heart was perfused with oxygenated Krebs-Henseleit solution, using the Lanngendorff technique at a constant flow of 15 ml per minute with a diastolic perfusion pressure greater than 50 mm Hg. The perfusate was previously equilibrated and constantly aerated with 95% 0$_2$ and 5% CO$_2$. The right ventricle was stimulated with square waves of 1 V for 1 ms every 500 ms (Pulsar 6I stimulator, Frederick Haer & Co., Brunswick, Me.). Following a 30 min. equilibration, the left atrium was incised to permit the insertion into the left ventricle of a balloon-tipped catheter which was inflated at a resting pressure of 20 mm Hg. Left ventricular pressure was measured using a Statham pressure transducer (Gould P230 ID) and recorded on a Gould polygraph (Model 2900, Gould, Cleveland, Ohio).

The preparation was allowed to stabilize for 30 min. prior to commencement of the experimental protocol. After obtaining baseline measurements, myocardial ischemia was produced by decreasing the perfusate flow to 2.5 ml per minute (80% of control) and by using an anoxic solution (95% N$_2$ and 5% CO$_2$). The period of ischemia and hypoxia (hereinafter referred to as "the ischemic period") lasted 45 minutes. Perfusion rate and oxygenation were then returned to control levels. Left ventricular pressure measurements were recorded before, during, and for 120 min. after myocardial ischemia.

One group of isolated rat hearts was pretreated with a 20 mer (SEQ. ID NO. 6). The 20 mer (SEQ. ID NO. 6) was added to the perfusate and hearts were perfused starting 15 minutes before reperfusion and continuing for 5–10 minutes after reperfusion. Left ventricular developed pressure was measured and compared to a control group of isolated rat hearts receiving no pretreatment. Left ventricular developed pressure, an index of left ventricular performance, is the difference between peak systolic pressure and resting left ventricular pressure. The results of this experiment are plotted in FIG. 1. Hearts pretreated with the 20 mer peptide (SEQ. ID NO. 6) experienced a rapid recovery.

Example 5

Amelioration of Cell Death in Spinal Cord Cells

This example serves to demonstrate the effectiveness of the peptides of the present invention to ameliorate neuronal cell death. Spinal cord cells isolated from embryonic chicks were grown in culture for 5–7 days. Chick spinal cord cells were cultured as described briefly as follows- Cell cultures were prepared from 7-day chick embryo. Ventral portions of spinal cord were dissected free of meninges and dorsal root ganglia and diced into small pieces in Dulbecco's phosphate-buffered saline (PBS). Tissue fragments were incubated in PBS with 0.25% trypsin and 20 ug/ml DNase for 30 min at 36° C. Trypsin was inactivated by the addition of horse serum and cells were dissociated by gentle pipetting.

Isolated cells were washed, resuspended in medium and plated onto plastic coverslips in petri dishes. The medium consisted of Eagle's minimum essential medium (MEM), 10% fetal bovine serum (FBS), 5 mg/ml D-glucose and 25 $\mu$g/ml gentamycin. Cells were grown in an incubator with 5% $CO_2$/95% air at 37° C. and the medium was renewed twice a week. Cells were used for experiment after 14 days.

Figure 2:
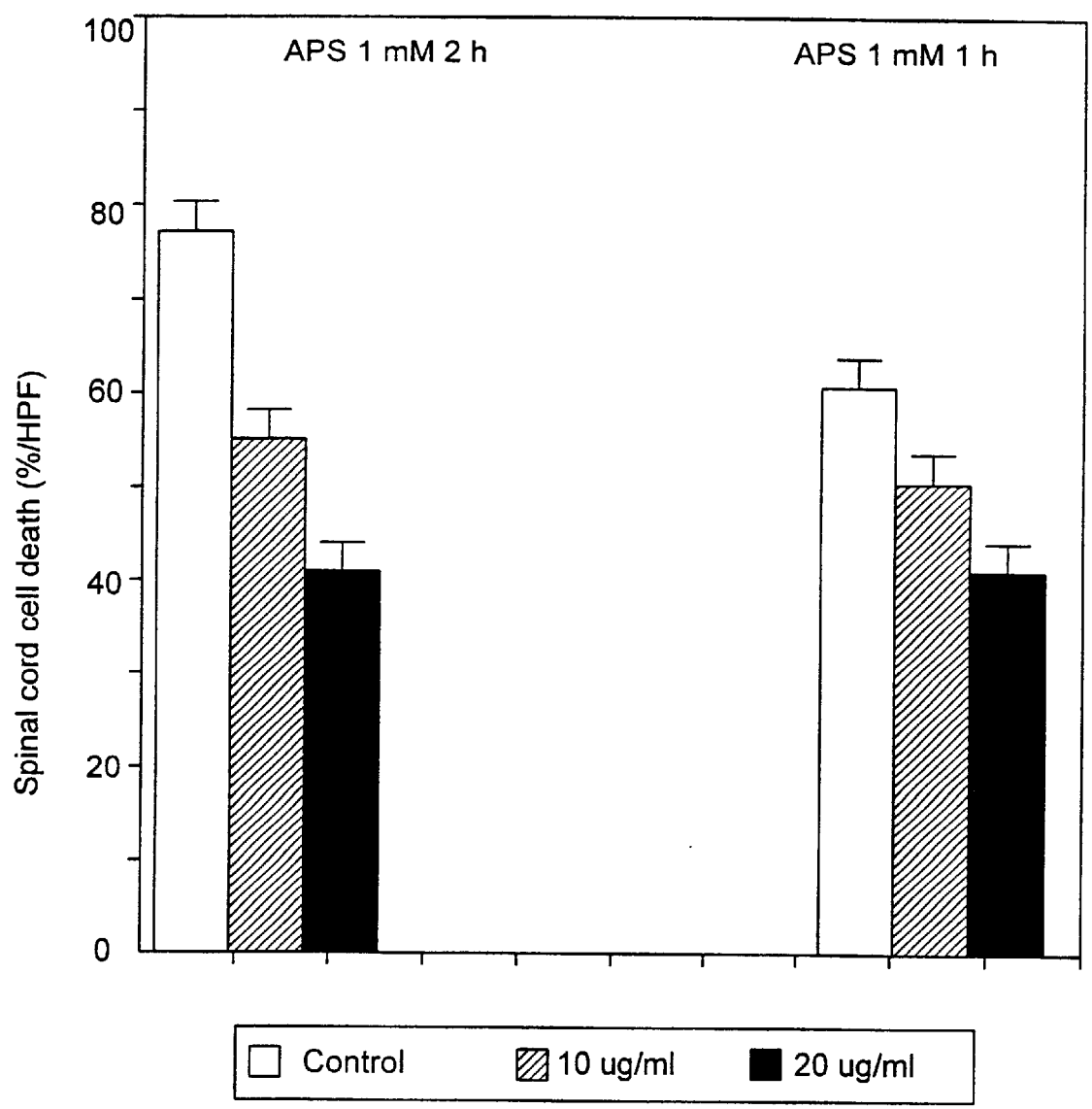
FIG. 2 is a bar graph which depicts survival of spinal cord cells exposed to ammonium persulfate, 1 mM for 2 hours (left) and for 1 hour (right). Cells pretreated with the 20 mer (SEQ. ID. No. 6) had much better survival, i.e., less death. Indeed, the 20 mer almost completely prevented cell death, compared to the number of dead cells observed in the absence of ammonium persulfate.

Both the experimental and control cultures were treated with 1 mM ammonium persulfate for 1 or 2 hours at 37° C. The experimental cultures were treated with either 10 $\mu$g/ml or 20 $\mu$g/ml of the 20 mer peptide (SEQ. ID NO. 6) for the same length of time. Results of two experiments, each carried out in duplicate, are shown in FIG. 2. The number of dead cells, assayed by trypan blue, in the experimental groups was compared to that in the control group. Pretreatment with the 20 mer peptide (SEQ. ID NO. 6) dramatically enhanced cell survival.

Example 6

Amerlioration of Cell Death in Human Hematopoietic Cell Lines

This example serves to demonstrate the use of the compounds of the present invention in ameliorating serum-deprivation-induced cell death.

The hematopoietic, growth factor dependent cell lines, M07E and TF-1 (Mijajima, CDNAX Research Institute, Palo Alto, Calif.), were starved for 30 hours in DMEM containing 1% fetal calf serum (Hyclone, Logan, Utah) in the presence or absence of 20 $\mu$g/ml of the 20 mer peptide (SEQ. ID NO. 6). Cell viability was measured by one of two methods, trypan blue exclusion or $^3$H-thymidine incorporation (Alai et al., *J. Biol. Chem.* 267:18021–18025, 1992).

Cells in the latter group were washed free of the 20 mer (SEQ. ID NO. 6), given saturating concentrations of growth factor (5 ng/ml of human interleukin-3) and incubated for an additional 22 hours. After the 22 hours, 1 $\mu$Ci of $^3$H-thymidine (2 Ci/mmol) was added and, after 2 hours, the cellular contents were harvested onto filtermats. Then $^3$H-thymidine incorporation was measured using an LKB Betaplate Harvester and liquid scintillation counter. The results of this experiment are presented in Tables 4 and 5. Note the increased viability of cells treated with the 20 mer peptide (SEQ. ID NO. 6).

TABLE 4

TRYPAN BLUE COUNTS (% VIABILITY)

| Cell Line | Control | 20 $\mu$g/ml 20 mer Peptide |
|---|---|---|
| M07E | 11 ± 1% | 20 ± 0.5% |
| TF-1 | 6 ± 1% | 29 ± 1% |

TABLE 5

$^3$H-THYMIDINE COUNTS (COUNTS PER MINUTE)

| Cell Line | Control | 20 $\mu$g/ml 20 mer Peptide |
|---|---|---|
| M07E | 2,003 ± 468 | 4,282 ± 212 |
| TF-1 | 14,728 ± 2,825 | 32,701 ± 5,565 |

Example 7

Animakl Model of Cornoary Artery Occlusion and Reperfusion

Peptides, peptide analogues and organic-molecule analogues of the present invention may be readily tested for their ability to treat, prevent, or other ameliorate apoptosis in vivo, utilizing a standard rat model of ligation/reperfusion.

Briefly, male Sprague-Dawley rats (250 to 300 gr) are anesthetized with 5% halothane/100% oxygen. The animals are intubated and ventilated with 1/5% halothane/100% oxygen using a rodent respirator. An incision is made in the skin on the left side of the chest, and the pectoral muscles retracted to expose the ribs. An incision is made through the fourth intercostal space, and the ribs spread to expose the heart. A ligature is placed under the left main coronary artery, which is tied off with a slip-knot. The chest is then briefly compressed to expel intraleural air. The skin incision is then closed using surgical clips, leaving one end of the coronary suture protruding from the chest. The animals are then ventilated with room air, and after 45 minutes of occlusion, the coronary artery is reperfused by pulling on the exteriorized suture to release the knot and remove the suture.

At the end of the reperfusion or permanent occlusion, the rats are anesthetized with sodium pentobarbital, and the abdomen opened. One milliliter of Evans blue dye (5% in saline) is injected into the vena cava to stain the area of the myocardium perfused by patent coronary arteries, thereby delineating the ischemic region by negative staining. Analysis is undertaken of neutrophil content, DNA fragmentation, and in situ end labeling (see generally, Fliss and Gattinger, *Cir. Res.* 79:949–956, 1996).

Peptides and peptide analogues which are administered either prior to, during, or subsequent to ligation and/or reperfiision, and which alter, in a statistically significant manner, the extent of apoptosis within the myocardium, may be utilized to treat a wide variety of coronary diseases where apoptosis occurs.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. An isolated peptide obtained from streptokinase, or a derivative or analog thereof, which ameliorates cell death.

2. The isolated peptide according to claim 1 wherein said peptide comprises the amino acid motif: Val-Asp-Val.

3. The isolated peptide according to claim 1 having the sequence as set forth in SEQ. ID. No. 1.

4. The isolated peptide according to claim 1 having the sequence as set forth in SEQ. ID. No. 2.

5. The isolated peptide according to clai 1 having the sequence as set forth in SEQ. ID. No. 3.

6. The isolated peptide according to claim 1 having the sequence as set forth in SEQ. ID. No. 4.

7. The isolated peptide according to claim 1 having the sequence as set forth in SEQ. ID. No. 5.

8. The isolated peptide according to claim 1 having the sequence as set forth in SEQ. ID. No. 6.

9. The isolated peptide according to claim 1 having the sequence as set forth in SEQ. ID. No. 7.

10. The isolated peptide according to claim 1 having the sequence as set forth in SEQ. ID. No. 8.

11. The isolated peptide according to claim 1 wherein said peptide is a cyclic peptide.

12. The isolated peptide according to claim 1 wherein said peptide contains one or more D amino acids.

13. The isolated peptide according to claim 1 wherein said peptide is further conjugated to one or more polypeptides.

14. The isolated peptide according to claim 1 wherein said peptide is conjugated to a non-peptide moiety.

15. The isolated peptide according to claim 14 wherein said non-peptide moiety is a sugar.

16. The isolated peptide according to claim 1 wherein said peptide flrtler comprises an end group cap.

17. The isolated peptide according to claim 16 wherein said end group cap is an ester.

18. The isolated peptide according to claim 16 wherein said end group cap is an amide.

19. The isolated peptide according to claim 1 wherein said peptide is from 3 to 20 amino acids in length.

* * * * *

UNITED STATES PATENT AND TRADEMARK OFFICE
CERTIFICATE OF CORRECTION

PATENT NO.    : 6,348,567 B1
DATED         : February 19, 2002
INVENTOR(S)   : Gerald Krystal and Simon W. Rabkin It is certified that error appears in the above-identified patent and that said Letters Patent is hereby corrected as shown below:

<u>Title page,</u>
Item [54], title, delete "PEPTIDES AND THEIR USE TO AMELIORATE CELL DEATH" and replace with -- NOVEL PEPTIDES AND THEIR USE TO AMELIORATE CELL DEATH --;

<u>Column 3,</u>
Line 65, delete "Q=glutarnine" and replace with -- Q=glutamine --;

<u>Column 6,</u>
Line 22, delete "see, for" and replace with -- (see, for --;

<u>Column 7,</u>
Line 28, delete "affmity" and replace with -- affinity --;

<u>Column 8,</u>
Line 58, delete "Prokarvotic" and replace with -- Prokaryotic --;
Line 61, delete "Eukarvotic" and replace with -- Eukaryotic --;

<u>Column 10,</u>
Line 16, delete "inventions" and replace with -- invention --;

<u>Column 11,</u>
Line 62, delete "glomerulonepliritis" and replace with -- glomerulonephritis --;

<u>Column 12,</u>
Line 24, delete "hyperthermnia" and replace with -- hyperthermia --;
Line 30, delete "infaction" and replace with -- infarction --;
Line 44, delete "CrohI's" and replace with -- Crohn's --;

<u>Column 15,</u>
Line 13, delete "seqence" and replace with -- sequence --;
Line 15, delete "seequencer" and replace with -- sequencer --;
Line 53, delete "Irelevant #3" and replace with -- Irrelevant #3 --;
Line 53, delete "ThE-AMIDE" and replace with -- TLE-AMIDE --;

<u>Column 17,</u>
Line 17, delete "follows-Cell" and replace with -- follows. Cell" --;

UNITED STATES PATENT AND TRADEMARK OFFICE
CERTIFICATE OF CORRECTION

PATENT NO. : 6,348,567 B1
DATED : February 19, 2002
INVENTOR(S) : Gerald Krystal and Simon W. Rabkin It is certified that error appears in the above-identified patent and that said Letters Patent is hereby corrected as shown below:

<u>Column 18,</u>
Line 25, delete "Coarnory" and replace with -- Coronary --;
Line 25, delete "Animakl" and replace with -- Animal --;
Line 58, delete "reperfiision" and replace with -- reperfusion --;

<u>Column 27,</u>
Line 20, delete "clai 1" and replace with -- claim 1 --;

<u>Column 28,</u>
Line 23, delete "flrtlr" and replace with -- further --.

Signed and Sealed this

Twenty-ninth Day of October, 2002

*Attest:*

JAMES E. ROGAN
*Attesting Officer*      *Director of the United States Patent and Trademark Office*